United States Patent
Tachikawa et al.

(10) Patent No.: US 8,153,989 B2
(45) Date of Patent: Apr. 10, 2012

(54) CHARGED PARTICLE BEAM IRRADIATING APPARATUS

(75) Inventors: Toshiki Tachikawa, Niihama (JP); Toru Asaba, Niihama (JP); Toshiaki Ochi, Niihama (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 420 days.

(21) Appl. No.: 12/382,919

(22) Filed: Mar. 26, 2009

(65) Prior Publication Data

US 2010/0072389 A1 Mar. 25, 2010

(30) Foreign Application Priority Data

Mar. 28, 2008 (JP) ................................ P2008-087123

(51) Int. Cl.
*H01J 3/26* (2006.01)
(52) U.S. Cl. ................................................. 250/396 R
(58) Field of Classification Search ............... 250/492.2, 250/398, 397, 505.1, 492.3; 850/9; 355/18, 355/73
See application file for complete search history.

(56) References Cited

U.S. PATENT DOCUMENTS

| | | | | |
|---|---|---|---|---|
| 4,421,988 | A * | 12/1983 | Robertson et al. | 250/492.2 |
| 5,933,211 | A * | 8/1999 | Nakasugi et al. | 355/18 |
| 6,172,363 | B1 * | 1/2001 | Shinada et al. | 850/9 |
| 6,304,320 | B1 * | 10/2001 | Tanaka et al. | 355/73 |
| 6,433,349 | B2 * | 8/2002 | Akiyama et al. | 250/505.1 |
| 7,619,229 | B2 * | 11/2009 | Nunan et al. | 250/492.21 |
| 2007/0189436 | A1 * | 8/2007 | Goto et al. | 378/4 |
| 2008/0087844 | A1 * | 4/2008 | Nunan et al. | 250/492.2 |
| 2010/0059688 | A1 * | 3/2010 | Claereboudt et al. | 250/397 |
| 2010/0243911 | A1 * | 9/2010 | Fujii et al. | 250/400 |

FOREIGN PATENT DOCUMENTS

JP 2002-22900 1/2002

* cited by examiner

*Primary Examiner* — Jack Berman
*Assistant Examiner* — Johnnie Smith
(74) *Attorney, Agent, or Firm* — Squire Sanders (US) LLP

(57) ABSTRACT

The present invention provides a charged particle beam irradiating apparatus capable of simply preventing unevenness or reduction in a peripheral portion of the dose distribution of a charged particle beam.

A charged particle beam irradiating apparatus includes scanning electromagnets that scan a charged particle beam and a control device that controls the operations of the scanning electromagnets. In the charged particle beam irradiating apparatus, the control unit changes a scanning speed when the charged particle beam is irradiated along an irradiation line such that a peripheral portion of the dose distribution of the charged particle beam is corrected.

6 Claims, 10 Drawing Sheets

Fig.6
(a)
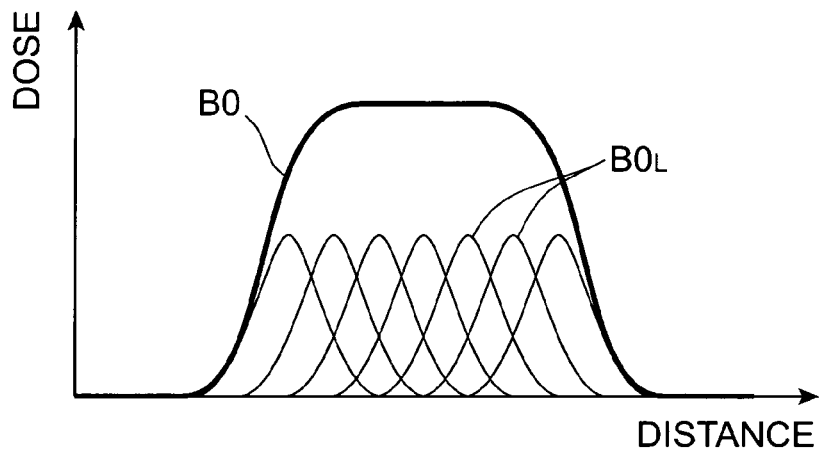
(b)
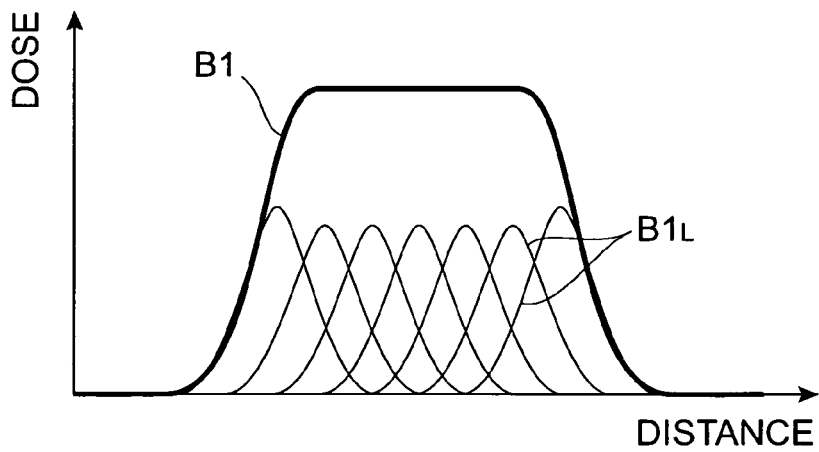
(c)
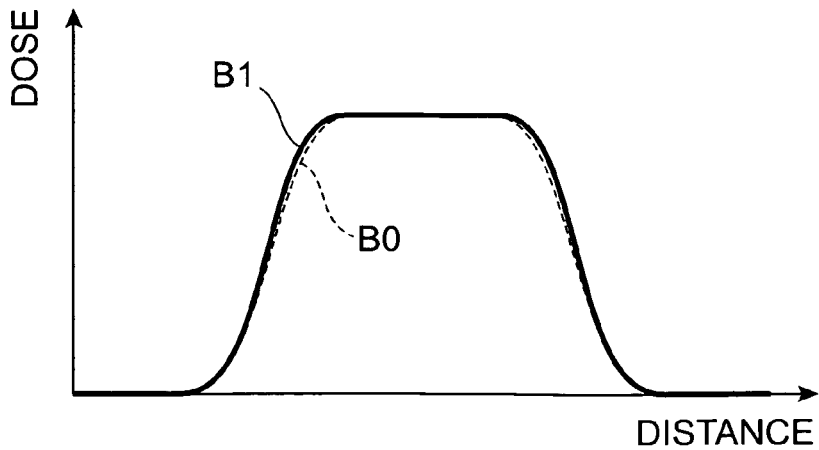

Fig.7
(a)
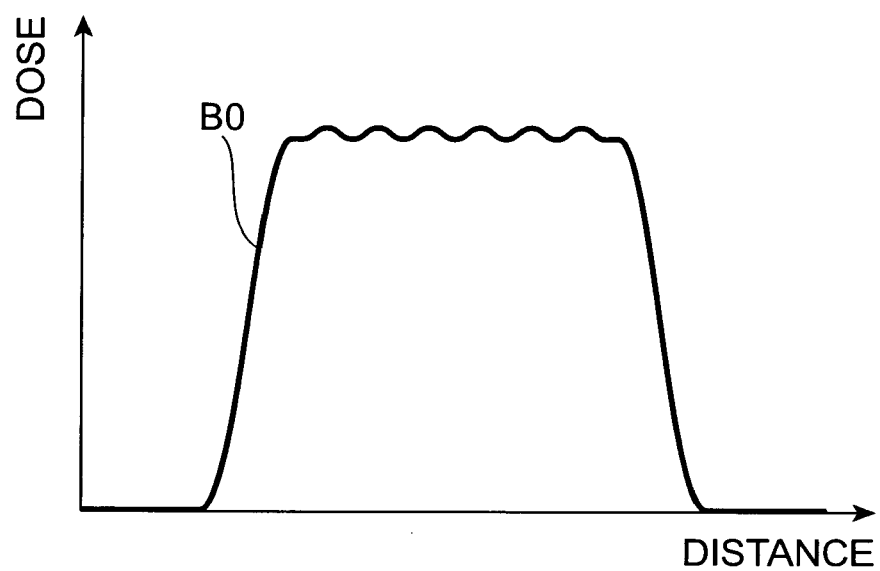
(b)
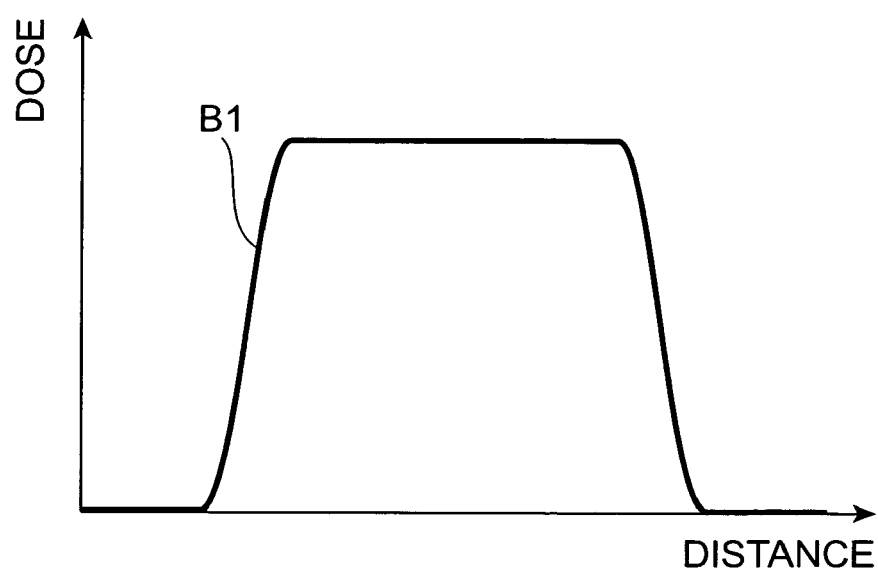

Fig.9
(a)
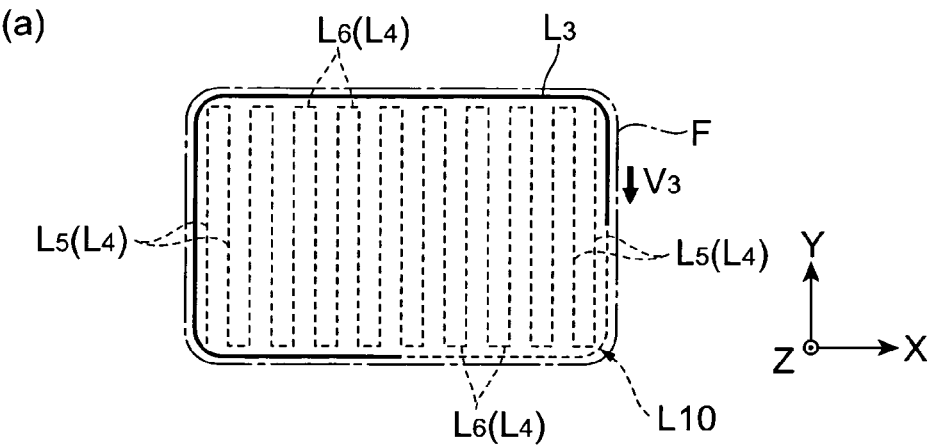
(b)
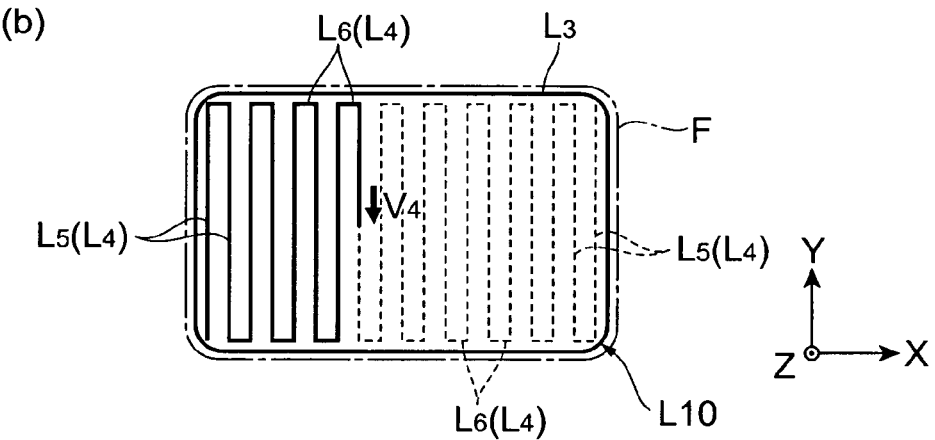
(c)
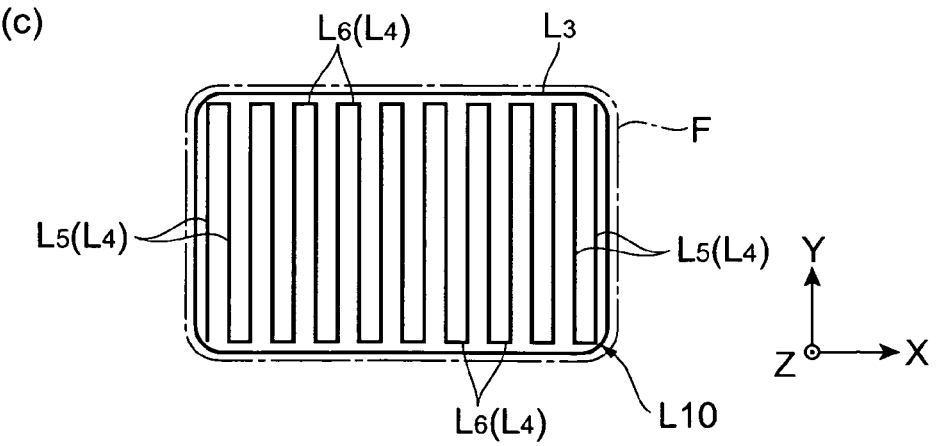

Fig.10
(a)
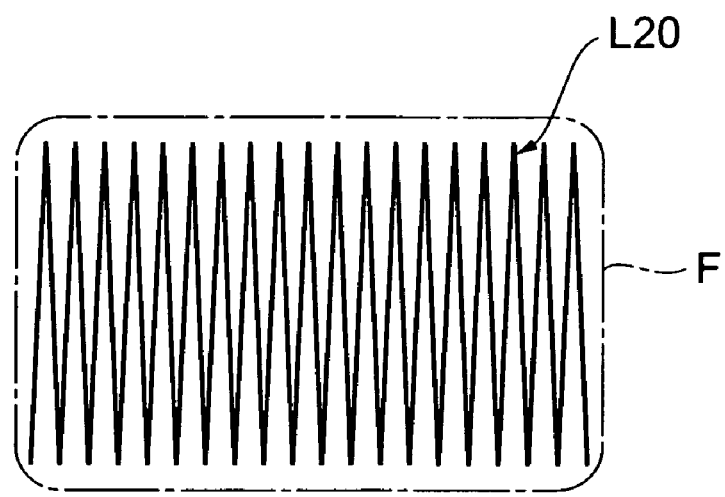
(b)
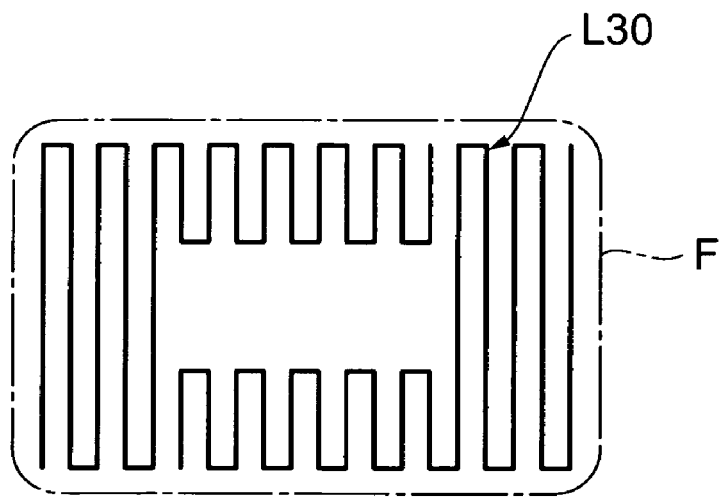

CHARGED PARTICLE BEAM IRRADIATING APPARATUS

BACKGROUND OF THE INVENTION

1. Field of the Invention

The present invention relates to a charged particle beam irradiating apparatus using a scanning method.

Priority is claimed on Japanese Patent Application No. 2008-87123, filed Mar. 28, 2008, the content of which is incorporated herein by reference.

2. Description of the Related Art

For example, JP-A-2002-22900 discloses a charged particle beam irradiating apparatus using a scanning method. The charged particle beam irradiating apparatus includes a scanning electromagnet that scans a charged particle beam and a control unit that controls the operation of the scanning electromagnet, and continuously irradiates the charged particle beam along an irradiation line in an irradiation field that is set in an object to scan the irradiation field.

However, in the above-mentioned charged particle beam irradiating apparatus, there is a concern that unevenness or reduction will occur in a peripheral portion of the dose distribution of the irradiated charged particle beam (hereinafter, simply referred to as a 'dose distribution'). It is considered to control the intensity of the charged particle beam to prevent the occurrence of the unevenness or reduction in the peripheral portion of the dose distribution. However, in this case, the scanning method needs to control the intensity of the charged particle beam at a high speed, and the control process is complicated. Therefore, the above-mentioned method is not effective.

SUMMARY OF THE INVENTION

Therefore, an object of the invention is to provide a charged particle beam irradiating apparatus capable of simply preventing unevenness or reduction in a peripheral portion of the dose distribution of a charged particle beam.

According to an aspect of the invention, there is provided a charged particle beam irradiating apparatus for continuously irradiating a charged particle beam along an irradiation line in an irradiation field that is set in an object. The charged particle beam irradiating apparatus includes: a scanning electromagnet that scans the charged particle beam; and a control unit that controls an operation of the scanning electromagnet. The control unit changes a scanning speed when the charged particle beam is irradiated along the irradiation line such that a peripheral portion of a dose distribution of the charged particle beam is corrected.

In the charged particle beam irradiating apparatus, the scanning speed when the charged particle beam is irradiated along the irradiation line is changed such that the peripheral portion of the dose distribution of the charged particle beam is corrected. That is, the irradiation time of the charged particle beam is increased or decreased such that the peripheral portion of the dose distribution is corrected. Therefore, it is possible to control the peripheral portion of the dose distribution without controlling the intensity of the charged particle beam. As a result, it is possible to simply prevent unevenness or reduction in the peripheral portion of the dose distribution.

The irradiation line may extend in a rectangular wave shape, and include a plurality of first irradiation lines that are arranged in parallel to each other at predetermined intervals and a plurality of second irradiation lines that connect the ends of adjacent first irradiation lines at one side or the other side. The 'rectangular wave shape' means a substantially rectangular wave shape as well as a completely rectangular wave shape.

The control unit may control a scanning speed when the charged particle beam is irradiated along an outermost first irradiation line among the plurality of first irradiation lines to be lower than a scanning speed when the charged particle beam is irradiated along the other first irradiation lines. In general, the dose of the charged particle beam has a Gaussian distribution. Therefore, since the dose distribution is likely to spread toward the bottom in an outer peripheral portion, the steepness of the dose distribution is likely to be lowered. In contrast, in the charged particle beam irradiating apparatus according to the above-mentioned aspect, as described above, the scanning speed when the charged particle beam is irradiated along the outermost first irradiation line among the first irradiation lines is set to be lower than the scanning speed when the charged particle beam is irradiated along the other first irradiation lines. Therefore, the charged particle beam is sufficiently irradiated along the outermost first irradiation line. As a result, it is possible to simply prevent the dose distribution from being reduced in the peripheral portion in a direction in which the first irradiation lines are arranged in parallel to each other.

The control unit may control a scanning speed when the charged particle beam is irradiated to an end of the first irradiation line to be lower than a scanning speed when the charged particle beam is irradiated to portions of the first irradiation line other than the end, or to be zero for a predetermined period of time. In this case, the charged particle beam is sufficiently irradiated to the end of the first irradiation line. Therefore, it is possible to simply prevent the dose distribution from being reduced in a peripheral portion in a direction along the first irradiation line.

The control unit may control a scanning speed when the charged particle beam is irradiated along the second irradiation line to be higher than the scanning speed when the charged particle beam is irradiated along the first irradiation line. When the irradiation line extends in a rectangular wave shape, an area in which the second irradiation line is arranged and an area in which no second irradiation line is arranged are mixed with each other at the end of the first irradiation line in the irradiation field. Therefore, the unevenness between an area in which the irradiation dose of the charged particle beam is large and an area in which the irradiation dose of the charged particle beam is small is likely to occur at the end of the first irradiation line in the irradiation field (for example, see FIG. 7A). However, in the invention, as described above, the scanning speed along the second irradiation line is set to be higher than the scanning speed along the first irradiation line. Therefore, it is possible to reduce the dose of the charged particle beam irradiated along the second irradiation line. As a result, it is possible to simply prevent the occurrence of unevenness between the area in which the dose of the charged particle beam is large and the area in which the dose of the charged particle beam is small at the end of the first irradiation line in the irradiation field (for example, see FIG. 7B).

The control unit may control a scanning speed when the charged particle beam is irradiated along the irradiation line in the peripheral portion of the dose distribution to be lower than a scanning speed when the charged particle beam is irradiated along the other irradiation lines. In this case, it is possible to simply prevent the dose distribution from being reduced in the peripheral portion.

The irradiation line may include a third irradiation line that extends along the edge of the irradiation field and a fourth irradiation line that is disposed inside the third irradiation line. The control unit may control a scanning speed when the charged particle beam is irradiated along the third irradiation line to be lower than a scanning speed when the charged particle beam is irradiated along the fourth irradiation line. In this case, the charged particle beam is sufficiently irradiated along the third irradiation line. Therefore, it is possible to simply prevent the dose distribution from being reduced in the peripheral portion.

The fourth irradiation line may extend in a rectangular wave shape, and include a plurality of fifth irradiation lines that are arranged in parallel to each other at predetermined intervals and a plurality of sixth irradiation lines that connect the ends of adjacent fifth irradiation lines on one side or the other side.

According to the above-mentioned aspect of the invention, it is possible to simply prevent unevenness or reduction in a peripheral portion of the dose distribution of a charged particle beam.

BRIEF DESCRIPTION OF THE DRAWINGS

FIGS. 6A to 6C are diagrams illustrating a dose distribution in a cross section taken along the line VI-VI of FIG. 5C;

FIGS. 7A and 7B are diagrams illustrating a dose distribution in a cross section taken along the line VII-VII of FIG. 5C;

FIGS. 9A to 9C are diagrams illustrating the operation of the charged particle beam irradiating apparatus according to the second embodiment of the invention; and FIGS. 10A and 10B are diagrams illustrating other examples of an irradiation line.

DESCRIPTION OF THE PREFERRED EMBODIMENTS

Figure 1:
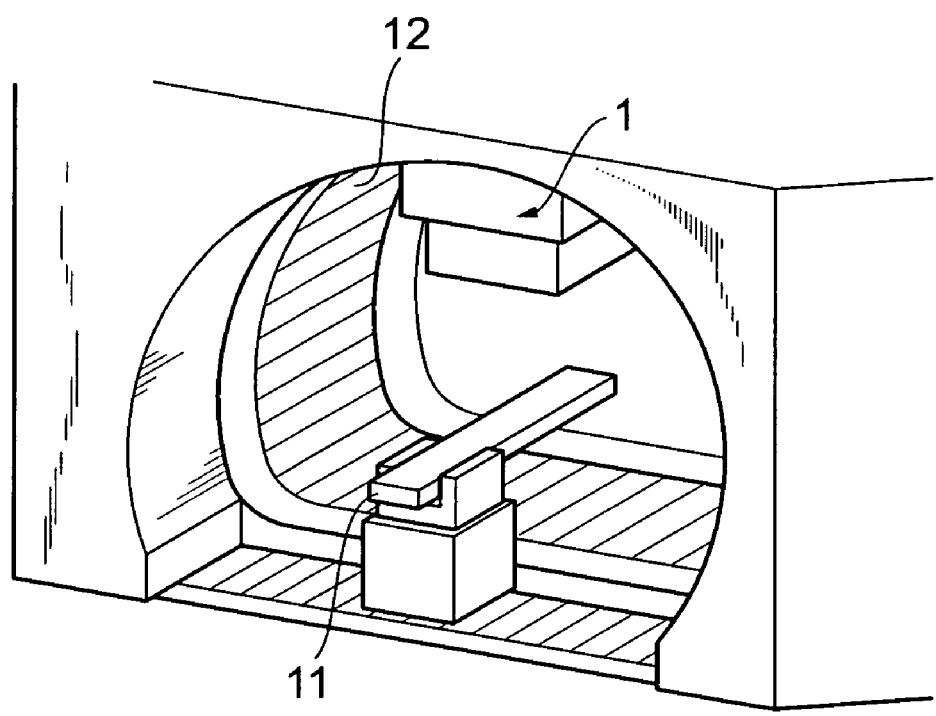
FIG. 1 is a perspective view illustrating a charged particle beam irradiating apparatus according to a first embodiment of the invention.

Hereinafter, exemplary embodiments of the invention will be described in detail with reference to the accompanying drawings. In the following description, the same or equivalent components are denoted by the same reference numerals, and a repetitive description thereof will be omitted.

Figure 2:
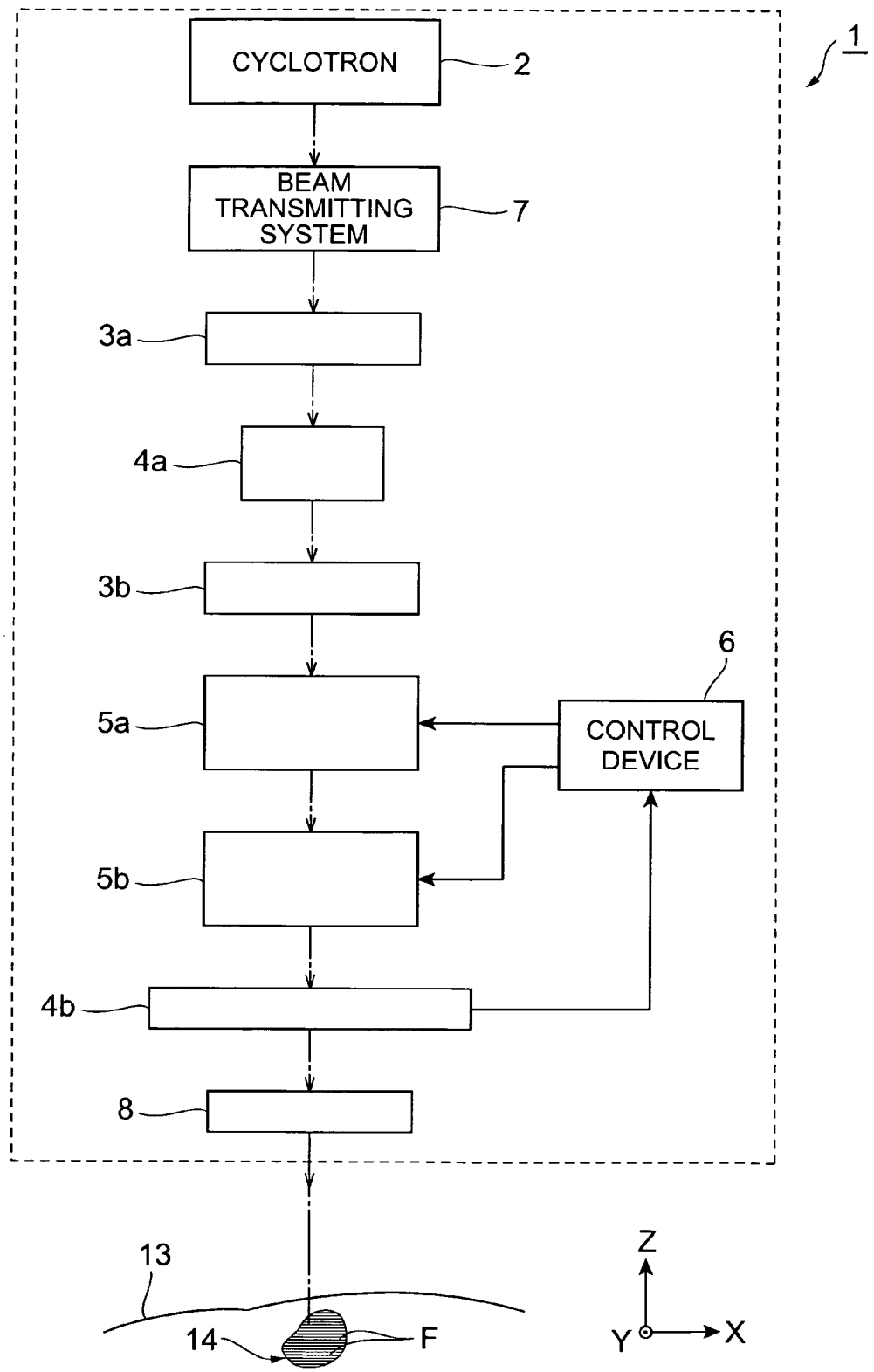
FIG. 2 is a diagram schematically illustrating the structure of the charged particle beam irradiating apparatus shown in FIG. 1.

First, a charged particle beam irradiating apparatus according to a first embodiment of the invention will be described. FIG. 1 is a perspective view illustrating the charged particle beam irradiating apparatus according to the first embodiment of the invention, and FIG. 2 is a diagram schematically illustrating the structure of the charged particle beam irradiating apparatus shown in FIG. 1. As shown in FIG. 1, a charged particle beam irradiating apparatus 1 uses a scanning method, and is provided on a rotating gantry 12 that is provided so as to surround a treatment table 11. The charged particle beam irradiating apparatus 1 can be rotated around the treatment table 11 by the rotating gantry 12.

As shown in FIG. 2, the charged particle beam irradiating apparatus 1 continuously irradiates a charged particle beam R to a tumor (object) 14 in the body of a patient 13. Specifically, the charged particle beam irradiating apparatus 1 divides a tumor 14 into a plurality of layers in the depth direction (Z direction), and continuously irradiates the charged particle beam R along an irradiation line L in an irradiation field F that is set in each of the layers at a scanning speed V to scan the irradiation field F (so-called line scanning). That is, the charged particle beam irradiating apparatus 1 divides the tumor 14 into a plurality of layers and performs planar scanning on each of the divided layers, in order to form a three-dimensional irradiation field corresponding to the tumors 14. In this way, the charged particle beam R is irradiated in correspondence with the three-dimensional shape of the tumor 14.

The charged particle beam R is obtained by accelerating charged particles at a high speed. For example, a proton beam, a heavy particle (heavy ion) beam, or an electron beam is used as the charged particle beam R. The irradiation field F is an area having a maximum size of, for example, 200 mm×200 mm. As shown in FIGS. 4A to 4D, in this embodiment, the irradiation field F has a substantially rectangular shape. The irradiation field F may have various shapes. For example, the irradiation field F may have a shape corresponding to the shape of the tumor 14.

The irradiation line L is a proposed line (virtual line) along which the charged particle beam R is irradiated. In this embodiment, the irradiation line L extends in a rectangular wave shape. Specifically, the irradiation line L includes a plurality of first irradiation lines $L_1$ ($L_{11}$ to $L_{1n}$, n is an integer) that are arranged in parallel to each other at predetermined intervals and a plurality of second irradiation lines $L_2$ each connecting the ends of adjacent first irradiation lines $L_1$ on one side or the other side.

Returning to FIG. 2, the charged particle beam irradiating apparatus 1 includes a cyclotron 2, convergence electromagnets 3a and 3b, monitors 4a and 4b, scanning electromagnets 5a and 5b, and a fine degrader 8. The cyclotron 2 is a generation source that continuously generates the charged particle beam R. The charged particle beam R generated by the cyclotron 2 is transmitted to the convergence electromagnet 3a in the next stage by a beam transmission system 7.

The convergence electromagnets 3a and 3b converge the charged particle beam R. The convergence electromagnets 3a and 3b are arranged on the downstream side of the cyclotron 2 in a direction in which the irradiation axis of the charged particle beam R (hereinafter, simply referred to as a 'radiation axis') extends.

The monitor 4a monitors the position of the charged particle beam R, and the monitor 4b monitors the absolute value of the dose of the charged particle beam R and the dose distribution of the charged particle beam R. For example, the monitor 4a is arranged between the convergence electromagnets 3a and 3b along the irradiation axis, and the monitor 4b is arranged on the downstream side of the convergence electromagnet 3b in the direction of the irradiation axis.

The scanning electromagnets 5a and 5b scan the charged particle beam R. Specifically, the scanning electromagnets 5a and 5b change a magnetic field according to a current applied to move the irradiation position of the charged particle beam R in the irradiation field. The scanning electromagnet 5a scans the charged particle beam R in the X direction (a direction orthogonal to the irradiation axis) of the irradiation field F, and the scanning electromagnet 5b scans the charged particle beam R in the Y direction (a direction orthogonal to the X direction and the irradiation axis) of the irradiation field F.

The scanning electromagnets 5a and 5b are arranged between the convergence electromagnet 3b and the monitor 4b in the direction of the irradiation axis. The scanning electromagnet 5a scans the charged particle beam R in the Y direction, and the scanning electromagnet 5b scans the charged particle beam R in the X direction.

The fine degrader 8 irradiates the charged particle beam R to each of the plurality of layers of the tumor 14 that are divided in the depth direction. Specifically, the fine degrader 8 changes the energy loss of the traveling charged particle beam R to adjust the penetration depth of the charged particle beam R in the body of the patient 13, thereby adjusting the penetration depth of the charged particle beam R in each of the divided layers.

The charged particle beam irradiating apparatus 1 further includes a control device (control unit) 6. The control device 6 is electrically connected to the monitor 4b and the scanning electromagnets 5a and 5b, and controls the operations of the scanning electromagnets 5a and 5b on the basis of the dose distribution and the absolute value of the dose of the charged particle beam R monitored by the monitor 4b (which will be described in detail below).

Figure 3:
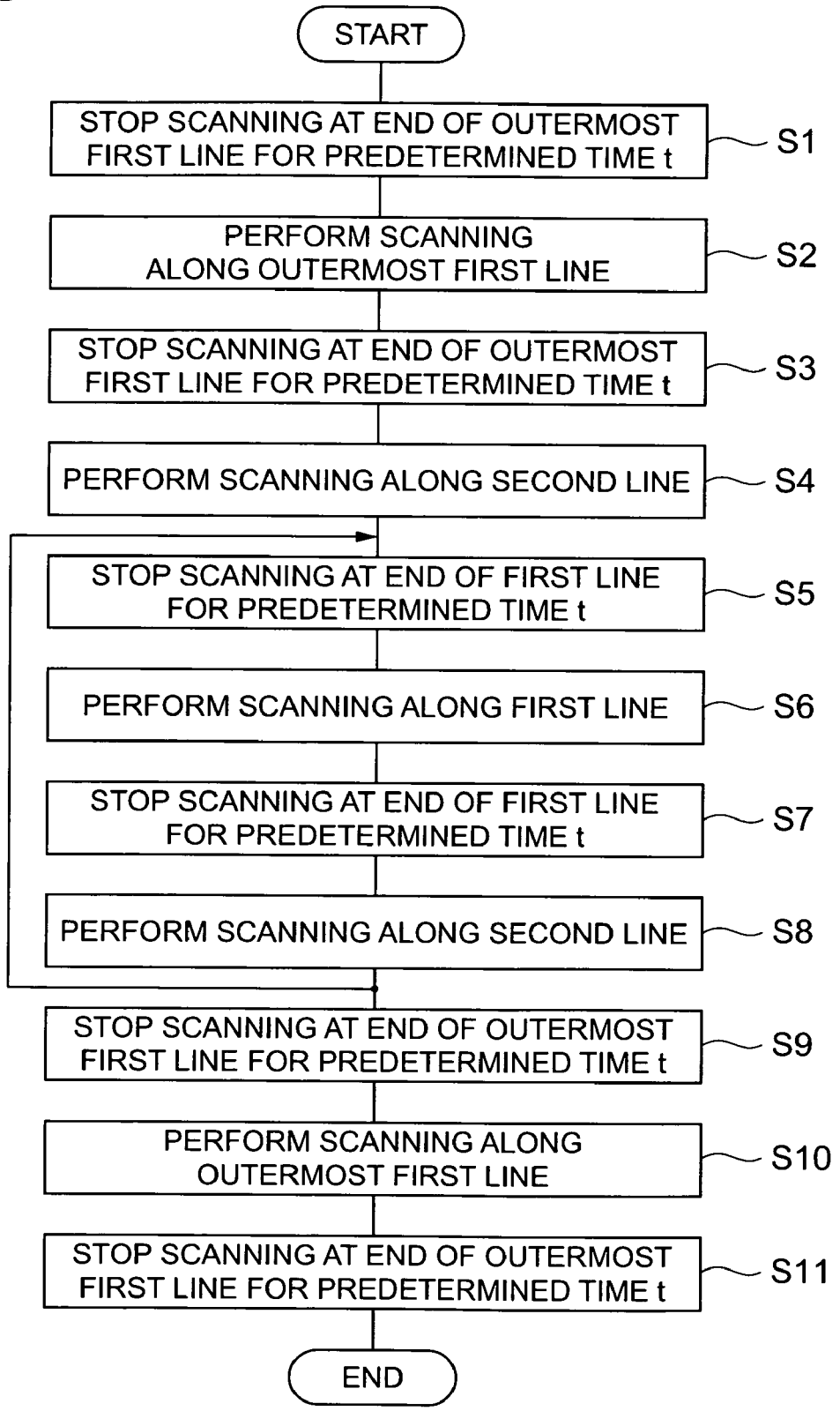
FIG. 3 is a flowchart illustrating the operation of the charged particle beam irradiating apparatus shown in FIG. 1.

Next, the operation of the charged particle beam irradiating apparatus 1 will be described with reference to a flowchart shown in FIG. 3.

The charged particle beam irradiating apparatus 1 divides the tumor 14 into a plurality of layers in the depth direction, and irradiates the charged particle beam R to the irradiation field F that is set in one of the layers. This operation is repeatedly performed on each of the layers to irradiate the charged particle beam R according to the three-dimensional shape of the tumor 14.

Figure 4:
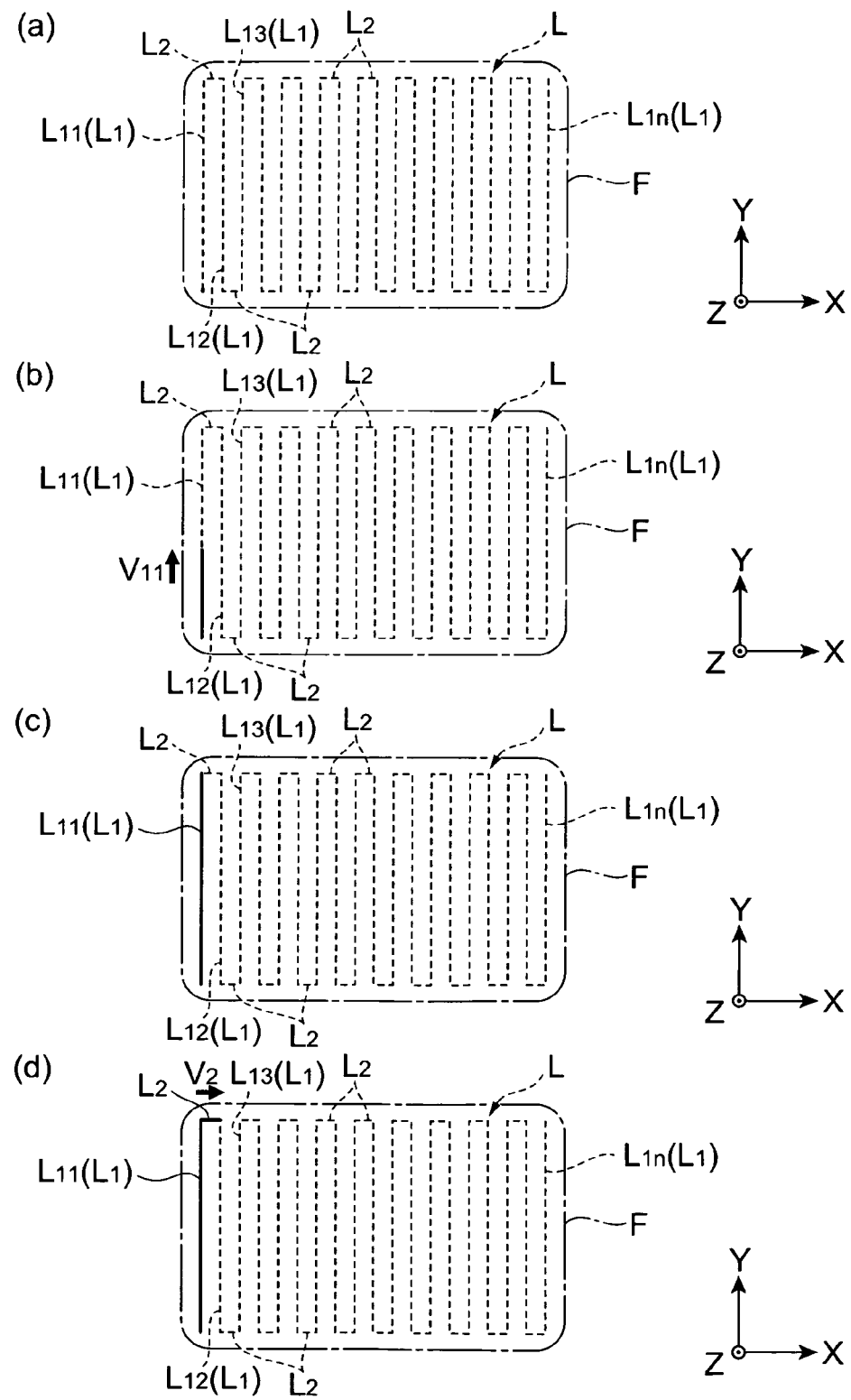
FIGS. 4A to 4D are diagrams illustrating the operation of the charged particle beam irradiating apparatus shown in FIG. 1.

When the charged particle beam R is irradiated, the control device 6 controls the scanning electromagnets 5a and 5b to scan the charged particle beam R in parallel along the irradiation line L in the irradiation field F and change the scanning speed such that a peripheral portion of a dose distribution (in this embodiment, an outer peripheral portion) is corrected. Specifically, the control device 6 controls the scanning electromagnets 5a and 5b to perform the following operation. That is, as shown in FIG. 4A, first, scanning stops (scanning speed is 0) for a predetermined time $t_1$ while the charged particle beam R is irradiated with its irradiation point aligned with one end of the outermost first irradiation line $L_{11}$ (the base end of the irradiation line L) (S1). The predetermined time $t_1$ is related to the half width D of the charged particle beam R and a scanning speed $V_{11}$, which will be described below, as represented by Expression 1 given below:

$$t_1 = \alpha_1 \times D/V_{11} \text{ (where } 0 < \alpha_1 < 1) \quad \text{[Expression 1]}$$

Then, as shown in FIG. 4B, the charged particle beam R is continuously irradiated along the first irradiation line $L_{11}$ at the scanning speed $V_{11}$ to scan the irradiation field (S2). Then, as shown in FIG. 4C, when the irradiation point of the charged particle beam R reaches the other end of the first irradiation line $L_{11}$, scanning with the charged particle beam R stops for the predetermined time $t_1$ (S3).

Then, as shown in FIG. 4D, the charged particle beam R is continuously irradiated along a second irradiation line $L_2$ at a scanning speed $V_2$ to scan the irradiation field (S4). The scanning speed $V_2$ is set to be higher than a scanning speed $V_{12}$, which will be described below. As shown in FIG. 4C, when the irradiation point of the charged particle beam R reaches the other end of the first irradiation line $L_{12}$, scanning with the charged particle beam R stops for a predetermined time $t_2$ (S5). The predetermined time $t_2$ is related to the half width D of the charged particle beam R and a scanning speed $V_{12}$, which will be described below, as represented by Expression 2 given below:

$$t_2 = \alpha_2 \times D/V_{12} \text{ (where } 0 < \alpha_2 < 1) \quad \text{[Expression 2]}$$

Figure 5:
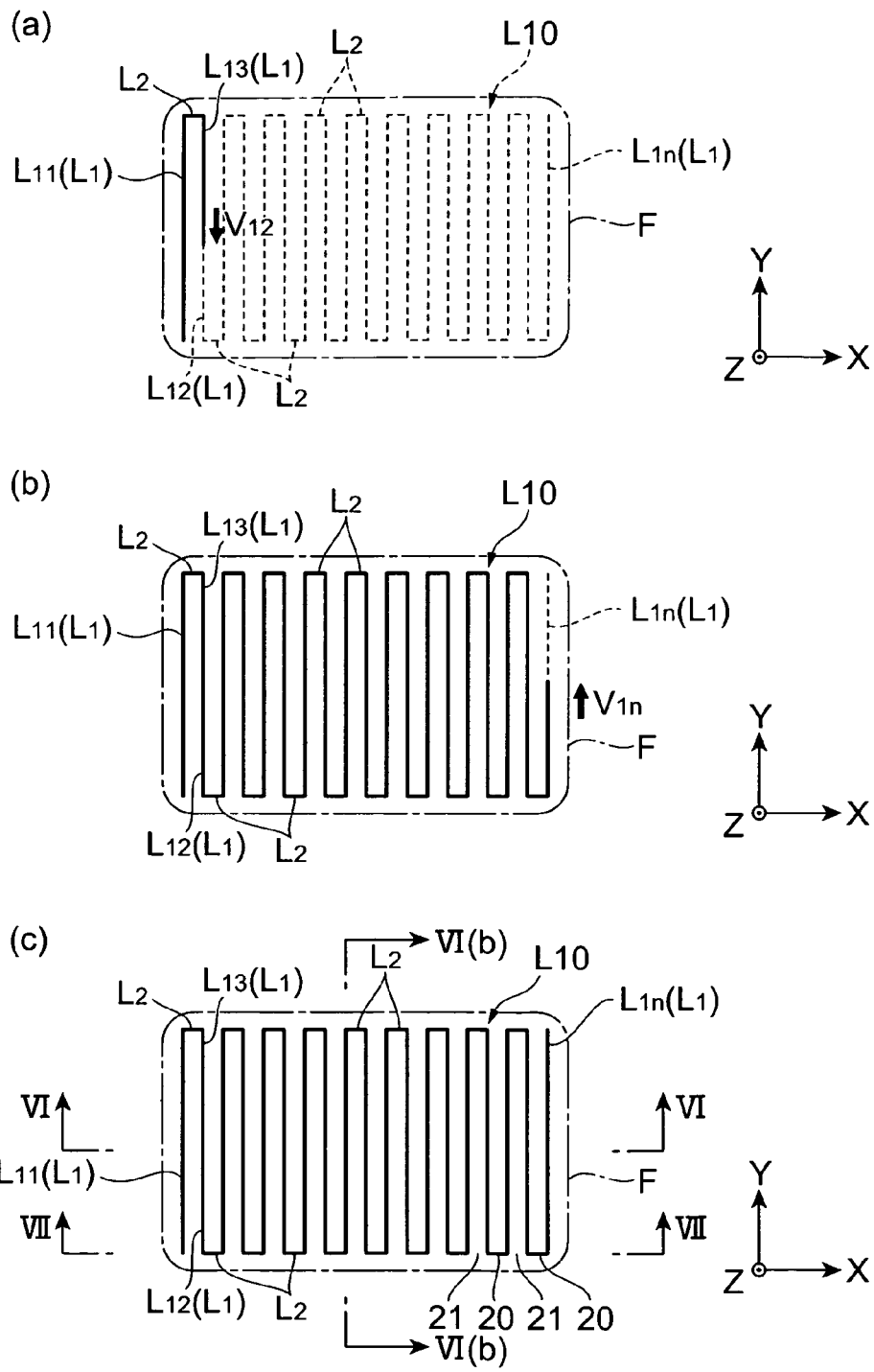
FIGS. 5A to 5C are diagrams following FIGS. 4A to 4D.

Then, as shown in FIG. 5A, the charged particle beam R is continuously irradiated along the first irradiation line $L_{12}$ at the scanning speed $V_{12}$ to scan the irradiation field (S6). The scanning speed $V_{12}$ is set to be higher than the scanning speed $V_{11}$. That is, the scanning speed $V_{11}$ along the first irradiation line $L_{11}$ is lower than the scanning speed $V_{12}$ along the first irradiation line $L_{12}$.

When the irradiation point of the charged particle beam R reaches one end of the first irradiation line $L_{12}$, scanning with the charged particle beam R stops for the predetermined time $t_2$ (S7). Then, the charged particle beam R is continuously irradiated along the second irradiation line $L_2$ at a scanning speed $V_2$ to scan the irradiation field (S8).

Then, Steps S5 to S8 are repeatedly performed a predetermined number of times. Thereafter, when the irradiation point of the charged particle beam R reaches one end of the first irradiation line $L_{1n}$ that is opposite to the first irradiation line $L_{11}$, scanning with the charged particle beam R stops for a predetermined time $t_n$ (S9). The predetermined time $t_n$ is related to the half width D of the charged particle beam R and a scanning speed $V_{1n}$, which will be described below, as represented by Expression 3 given below:

$$t_n = \alpha_n \times D/V_{1n} \text{ (where } 0 < \alpha_n < 1) \quad \text{[Expression 3]}$$

Then, as shown in FIG. 5B, the charged particle beam R is continuously irradiated along the first irradiation line $L_{1n}$ at the scanning speed $V_{1n}$ that is lower than the scanning speed $V_{12}$ to scan the irradiation field (S10). Finally, as shown in FIG. 5C, when the irradiation point of the charged particle beam R reaches the other end (the end of the irradiation line) of the first irradiation line $L_{1n}$, scanning with the charged particle beam R stops for the predetermined time $t_n$ (S11). In this way, the irradiation of the charged particle beam R along the irradiation line L in the irradiation field F is completed.

FIG. 6A is a diagram illustrating the dose distribution of a charged particle beam irradiating apparatus according to the related art. FIG. 6B is a diagram illustrating the dose distribution of the charged particle beam irradiating apparatus shown in FIG. 1. FIG. 6C is a diagram illustrating comparison between FIG. 6A and FIG. 6B. In FIGS. 6A to 6C, dose distributions B0 and B1 indicate the dose distributions (total dose distributions) of the charged particle beam R, and dose distributions $B0_L$ and $B1_L$ indicate only dose distributions along each irradiation line L.

The dose (intensity) of the charged particle beam R has a Gaussian distribution. Therefore, as shown in FIG. 6A, in the charged particle beam irradiating apparatus according to the related art, the dose distribution B0 is reduced in a peripheral portion (the steepness of the dose distribution B0 is lowered). That is, inside the dose distribution B0, uniformity can be maintained by the influence (overlap) of the charged particle beam R irradiated along adjacent irradiation lines L, but in the peripheral portion (outline), the dose distribution is slightly inclined and spread toward the bottom.

In contrast, in the charged particle beam irradiating apparatus 1 according to this embodiment, as described above, the control device 6 controls the scanning speeds $V_{11}$ and $V_{1n}$ when the charged particle beam R is irradiated along the outermost first irradiation lines $L_{11}$ and $L_{1n}$ among the first irradiation lines $L_1$ to be lower than the scanning speed $V_{12}$ when the charged particle beam R is irradiated along the other first irradiation lines. Therefore, the irradiation time of the charged particle beam R along the first irradiation lines $L_{11}$ and $L_{1n}$ is increased, and the charged particle beam R is sufficiently irradiated along the first irradiation lines $L_{11}$ and $L_{1n}$. As a result, as shown in FIGS. 6B and 6C, in the dose distribution B1 of the charged particle beam irradiating apparatus 1, the dose distribution B1 is sharply increased in a peripheral portion in a direction in which the first irradiation lines $L_1$ are arranged in parallel to each other (in the horizontal direction of FIGS. 4A to 4D), and it is possible to prevent the dose distribution from being reduced in the peripheral portion.

Further, in the charged particle beam irradiating apparatus 1, as described above, when the charged particle beam R is irradiated to the ends of the first irradiation line $L_1$ (one end and the other end), the control device 6 stops scanning with the charged particle beam R for the predetermined time $t_1$. Therefore, the irradiation time of the charged particle beam R at the end of the first irradiation line $L_1$ is increased, and the charged particle beam is sufficiently irradiated. As a result, the dose distribution B1 is sharply increased in a peripheral portion in a direction along the first irradiation line $L_1$ (in the vertical direction of FIGS. 4A to 4D), and it is possible to prevent the dose distribution from being reduced in the peripheral portion.

When the irradiation line L extends in a rectangular wave shape, as shown in FIG. 5C, an area 20 in which the second irradiation line $L_2$ is arranged and an area 21 in which no second irradiation line is arranged are mixed with each other at the end of the first irradiation line $L_1$ in the irradiation field F. Therefore, in the charged particle beam irradiating apparatus according to the related art, as shown in FIG. 7A, the unevenness between an area in which the irradiation dose of the charged particle beam R is large and an area in which the irradiation dose of the charged particle beam R is small is likely to occur at the end of the first irradiation line $L_1$ in the irradiation field F (spots are likely to occur).

In contrast, according to the charged particle beam irradiating apparatus 1, as described above, the control device 6 controls the scanning speed $V_2$ when the charged particle beam R is irradiated along the second irradiation line $L_2$ to be higher than the scanning speeds $V_{11}$, $V_{12}$, and $V_{1n}$ when the charged particle beam is irradiated along the first irradiation line $L_1$. Therefore, as shown in FIG. 7B, it is possible to reduce the dose of the charged particle beam R irradiated along the second irradiation line $L_2$. As a result, it is possible to prevent the occurrence of unevenness at the end of the first irradiation line $L_1$ in the irradiation field F.

As described above, according to the charged particle beam irradiating apparatus 1 of the first embodiment, the control device 6 changes the scanning speed V when the charged particle beam is irradiated along the irradiation line L such that a peripheral portion of the dose distribution of the charged particle beam R is corrected. Therefore, it is possible to control the peripheral portion of the dose distribution B1 without controlling the intensity of the charged particle beam R. As a result, it is possible to easily and simply prevent the occurrence of unevenness or reduction in a peripheral portion of the dose distribution B1.

Furthermore, as described above, the charged particle beam irradiating apparatus 1 includes the cyclotron 2 that continuously generates the charged particle beam R. This structure is effective in continuously irradiating the charged particle beam R along the irradiation line L, as compared to a structure including a synchrotron that generates the charged particle beam R discontinuously (in a pulse manner).

Next, a charged particle beam irradiating apparatus according to a second embodiment of the invention will be described. In the second embodiment, the difference between the charged particle beam irradiating apparatus according to this embodiment and the charged particle beam irradiating apparatus 1 according to the first embodiment will be mainly described.

As shown in FIGS. 9A to 9C, an irradiation line L10 includes a third irradiation line $L_3$ that extends along the edge of the irradiation field F and a fourth irradiation line $L_4$ that is disposed inside the third irradiation line $L_3$. In addition, the fourth irradiation line $L_4$ includes a fifth irradiation line $L_5$ that is the same as the irradiation line $L_1$ and a sixth irradiation line $L_6$ that is the same as the irradiation line $L_2$. The control device 6 controls the scanning electromagnets 5a and 5b to perform the following operation.

Figure 8:
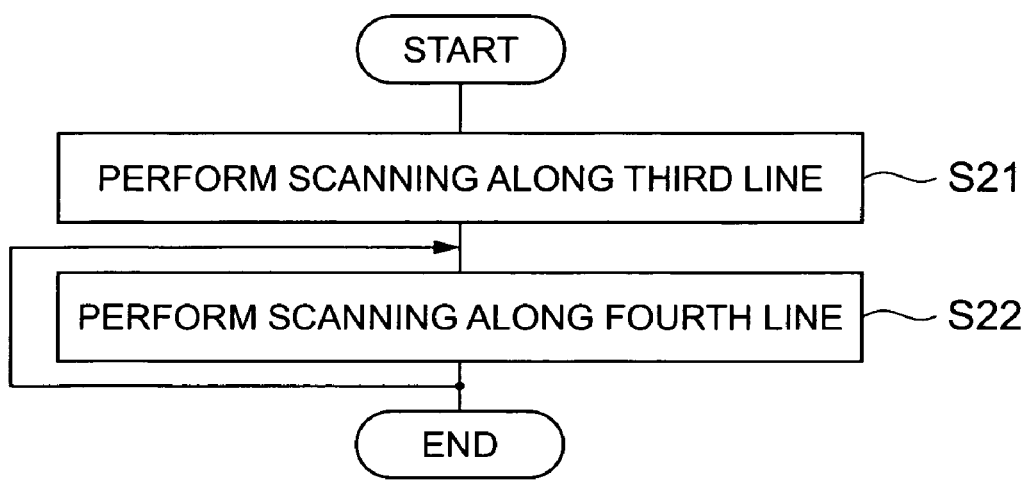
FIG. 8 is a flowchart illustrating the operation of a charged particle beam irradiating apparatus according to a second embodiment of the invention.

That is, first, as shown in FIG. 9A, the charged particle beam R is continuously irradiated along the third irradiation line $L_3$ at a scanning speed $V_3$ to scan the irradiation field (S21 of FIG. 8). The scanning speed $V_3$ is set to be lower than a scanning speed $V_4$, which will be described below.

Then, as shown in FIG. 9B, the charged particle beam R is continuously irradiated along the fourth irradiation line $L_4$ at the scanning speed $V_4$ to scan the irradiation field (S22). Specifically, the charged particle beam R is irradiated along the irradiation line $L_5$ at a scanning speed $V_{41}$ that is equal to the scanning speed $V_{12}$ to scan the irradiation field, and is then irradiated along the irradiation line $L_6$ at a scanning speed $V_{42}$ that is equal to the scanning speed $V_2$ to scan the irradiation field. Then, Step S22 is repeatedly performed a predetermined number of times to complete the irradiation of the charged particle beam R along the irradiation line L10 in the irradiation field F, as shown in FIG. 9C.

As described above, in the charged particle beam irradiating apparatus according to this embodiment, the control device 6 controls the scanning speed $V_3$ when the charged particle beam R is irradiated along the third irradiation line $L_3$ to be lower than the scanning speed $V_4$ ($V_{41}$ and $V_{42}$) when the charged particle beam R is irradiated along the fourth irradiation line $L_4$ that is disposed inside the third irradiation line $L_3$. That is, the control device 6 controls the scanning speed when the charged particle beam R is irradiated along an irradiation line in a peripheral portion of the dose distribution B1 to be lower than the scanning speed when the charged particle beam R is irradiated along the other irradiation lines. Therefore, the irradiation time of the charged particle beam R along the third irradiation line $L_3$ is increased, and the charged particle beam R is sufficiently irradiated along the third irradiation line $L_3$. As a result, it is possible to simply prevent the peripheral portion of the dose distribution B1 from being reduced.

Although the exemplary embodiments of the invention have been descried above, the invention is not limited to the embodiments.

For example, as shown in FIG. 10A, the charged particle beam R may be continuously irradiated along an irradiation line L20 that extends in a chopping wave shape in the irradiation field F to scan the irradiation field (so-called raster scanning). That is, the invention can be applied to irradiation lines with any shape. In addition, as shown in FIG. 10B, an irradiation line L30 may be set so as to avoid a portion of the irradiation field F (in this case, a central portion), and the charged particle beam R may be irradiated so as to avoid the portion of the irradiation field F. In this case, the peripheral portion of the dose distribution is an outer peripheral portion and an inner peripheral portion.

In the above-described embodiments, when the charged particle beam R is irradiated to one end and the other end of the first irradiation line $L_1$, scanning with the charged particle beam stops for a predetermined time. However, the scanning speed may be lowered without stopping the scanning. That is, the scanning speed at one end and the other end of the first irradiation line $L_{11}$ may be lower than the scanning speed $V_{11}$, and the scanning speed at one end and the other end of the first irradiation line $L_{12}$ may be lower than the scanning speed $V_{12}$. In addition, the scanning speed at one end and the other end of the first irradiation line $L_{1n}$ may be lower than the scanning speed $V_{1n}$.

The positions of the monitors 4a and 4b are not limited to those in the above-described embodiments, but they may be disposed at appropriate positions.

What is claimed is:

1. A charged particle beam irradiating apparatus for continuously irradiating a charged particle beam along an irradiation line in an irradiation field that is set in an object, comprising:
    a scanning electromagnet that scans the charged particle beam; and
    a control unit that controls an operation of the scanning electromagnet,
        wherein the control unit changes a scanning speed when the charged particle beam is irradiated along the irradiation line such that a peripheral portion of a dose distribution of the charged particle beam is corrected,
        wherein the irradiation line extends in a rectangular wave shape, and includes a plurality of first irradiation lines that are arranged in parallel to each other at predetermined intervals and a plurality of second irradiation lines that connect the ends of adjacent first irradiation lines on one side or the other side, and
        wherein the control unit controls a scanning speed when the charged particle beam is irradiated along an outermost first irradiation line among the plurality of first irradiation lines to be lower than a scanning speed when the charged particle beam is irradiated along the other first irradiation lines.

2. The charged particle beam irradiating apparatus according to claim 1,
    wherein the control unit controls a scanning speed when the charged particle beam is irradiated to an end of the first irradiation line to be lower than a scanning speed when the charged particle beam is irradiated to portions of the first irradiation line other than the end, or to be zero for a predetermined time.

3. The charged particle beam irradiating apparatus according to claim 1,
    wherein the control unit controls a scanning speed when the charged particle beam is irradiated along the second irradiation line to be higher than the scanning speed when the charged particle beam is irradiated along the first irradiation line.

4. A charged particle beam irradiating apparatus for continuously irradiating a charged particle beam along an irradiation line in an irradiation field that is set in an object, comprising:
    a scanning electromagnet that scans the charged particle beam; and
    a control unit that controls an operation of the scanning electromagnet,
        wherein the control unit changes a scanning speed when the charged particle beam is irradiated along the irradiation line such that a peripheral portion of a dose distribution of the charged particle beam is corrected, and
        wherein the control unit controls a scanning speed when the charged particle beam is irradiated along the irradiation line in the peripheral portion of the dose distribution to be lower than a scanning speed when the charged particle beam is irradiated along the other irradiation lines.

5. The charged particle beam irradiating apparatus according to claim 4,
    wherein the irradiation line includes a third irradiation line that extends along the edge of the irradiation field and a fourth irradiation line that is disposed inside the third irradiation line, and
    the control unit controls a scanning speed when the charged particle beam is irradiated along the third irradiation line to be lower than a scanning speed when the charged particle beam is irradiated along the fourth irradiation line.

6. The charged particle beam irradiating apparatus according to claim 5,
    wherein the fourth irradiation line extends in a rectangular wave shape, and includes a plurality of fifth irradiation lines that are arranged in parallel to each other at predetermined intervals and a plurality of sixth irradiation lines that connect the ends of adjacent fifth irradiation lines on one side or the other side.

* * * * *